United States Patent
Davis, III et al.

(10) Patent No.: US 8,034,073 B2
(45) Date of Patent: Oct. 11, 2011

(54) STRETCH RESISTANT EMBOLIC COIL

(75) Inventors: Richard Champion Davis, III, Plantation, FL (US); Elias Rodriguez, Miami, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 723 days.

(21) Appl. No.: 11/507,208

(22) Filed: Aug. 18, 2006

(65) Prior Publication Data

US 2008/0046093 A1 Feb. 21, 2008

(51) Int. Cl.
*A61M 29/00* (2006.01)
*A61F 2/06* (2006.01)

(52) U.S. Cl. .................................. 606/200; 623/1.11

(58) Field of Classification Search .................. 606/200, 606/213; 623/1.11, 1.22; 267/70, 71, 73, 267/74, 165, 168
See application file for complete search history.

(56) References Cited

U.S. PATENT DOCUMENTS

| | | | |
|---|---|---|---|
| 5,108,407 A | 4/1992 | Geremia | |
| 5,122,136 A | 6/1992 | Guglielmi | |
| 5,304,195 A | 4/1994 | Twyford, Jr. | |
| 5,334,210 A | 8/1994 | Gianturco | |
| 5,382,259 A | 1/1995 | Phelps | |
| 5,482,261 A * | 1/1996 | Ortega | 267/168 |
| 5,582,619 A * | 12/1996 | Ken | 606/191 |
| 5,853,418 A | 12/1998 | Ken et al. | |
| 6,068,644 A * | 5/2000 | Lulo et al. | 606/191 |
| 6,179,857 B1 | 1/2001 | Diaz et al. | |
| 6,280,457 B1 | 8/2001 | Wallace et al. | |
| 6,468,266 B1 | 10/2002 | Bashiri et al. | |
| 6,616,617 B1 * | 9/2003 | Ferrera et al. | 600/585 |
| 6,689,141 B2 * | 2/2004 | Ferrera et al. | 606/108 |
| 7,216,687 B2 * | 5/2007 | Franssen | 160/84.06 |
| 2004/0002733 A1 | 1/2004 | Teoh | |
| 2004/0006363 A1 | 1/2004 | Schaefer | |
| 2004/0034363 A1 | 2/2004 | Wilson | |
| 2005/0043755 A1 | 2/2005 | Wilson et al. | |
| 2005/0090861 A1 | 4/2005 | Porter | |
| 2005/0171572 A1 | 8/2005 | Martinez | |

FOREIGN PATENT DOCUMENTS

EP 0941701 A 9/1999

* cited by examiner

*Primary Examiner* — Anhtuan Nguyen
*Assistant Examiner* — Jocelin C Tanner

(57) ABSTRACT

A vasoocclusive embolic device deployment system for use in the placement of an embolic coil at a treatment site within a vessel. The embolic coil includes an elongated stretch resistant fiber having one distal end bonded to the distal end of the embolic coil. The stretch resistant fiber includes portions which take the form of periodic undulations separated by portions which are straight. The stretch resistant fiber extends through the lumen of the coil and the other distal end is bonded to the proximal end of the coil. The stretch resistant fiber may be attached to the embolic coil at additional points between the proximal and distal ends of the coil. Additionally, a headpiece is mounted on the proximal end of the embolic coil and serves to couple the embolic coil to a deployment catheter.

15 Claims, 2 Drawing Sheets

STRETCH RESISTANT EMBOLIC COIL

BACKGROUND OF INVENTION

1. Field of the Invention

The present invention relates to a medical device designed for implantation within a vessel of the body, and more particularly, to a stretch resistant vasoocclusive coil for the treatment of aneurysms. The vasoocclusive coil is particularly suited for use in cases where it may be necessary to reposition the coil once the coil has been initially placed within the vessel.

2. Description of the Prior Art

For many years, vasoocclusive devices have been used to occlude blood vessels at specific treatment locations. These devices take many different forms including helically wound coils, coils wound within coils, or other such coil configurations. Examples of various coil configurations are disclosed in U.S. Pat. No. 5,334,210, entitled "Vascular Occlusion Assembly;" and U.S. Pat. No. 5,382,259, entitled, "Vasoocclusion Coil with Attached Tubular Woven or Braided Fibrous Covering." Embolic coils are generally formed of a radiopaque metallic material, such as platinum, gold, tungsten, or an alloy of these metals. Often, several coils are placed at a given location to occlude, or partially occlude, the flow of blood through the vessel or aneurysm by promoting thrombus formation at the particular location.

Flexible catheters have been used to place various devices or medications within the vasculature of the human body. Such devices or medications include dilation balloons, radiopaque fluids, liquid medications, and various types of occlusion devices such as balloons and embolic coils. Examples of such catheter-based devices are disclosed in U.S. Pat. No. 5,108,407, entitled "Method and Apparatus for Placement of an Embolic Coil;" and U.S. Pat. No. 5,122,136, entitled "Endovascular Electrolytically Detachable Guidewire Tip for the Electroformation of Thrombus in Arteries, Veins, Aneurysms, Vascular Malformations and Arteriovenous Fistulas." These patents disclose catheter-based devices designed to deliver embolic coils to a predetermined site within a vessel of the human body in order to treat aneurysms, or alternatively, to occlude a blood vessel at a particular location.

Additionally, embolic coils have been placed within the distal end of a catheter, such that when the distal end of the catheter is properly positioned, the coil may then be pushed out of the end of the catheter with a pusher member to release the coil at the predetermined site within the vessel. This procedure for placement of the embolic coil is conducted under fluoroscopic visualization, such that the movement of a coil through the vasculature of the body may be monitored, and the coil may be placed in the desired location.

To prevent stretching of the embolic device, especially during post-deployment retrieval, or repositioning during delivery, embolic devices often take the form of an embolic coil having a lumen extending therethrough and a stretch resistant member extending through the lumen. In one embodiment, the stretch resistant member takes the form of a fiber which is attached to the proximal and distal ends of the coil. In another embodiment, the stretch resistant member is fixedly attached to the distal end of the embolic coil, is extended through the lumen of the coil, and is detachably connected to a proximal end of an elongated pusher member. The connection between the pusher member and the coil may be severed by application of heat to the stretch resistant member, typically formed of a thermoplastic material. Such a device is disclosed in U.S. Patent Publication No. 2004/0034363, entitled "Stretch Resistant Therapeutic Device."

Another variation of a stretch resistant embolic device includes a helically wound outer coil with a stretch resistant member extending therethrough. In order to prevent stretching during movement of the coil, the stretch resistant member is fixedly attached to the coil in at least two locations, such as the proximal end and the distal end. The coil may take on a secondary shape when it is released from the delivery device. Such a device is disclosed in U.S. Pat. No. 5,853,418, entitled "Stretch Resistant Vaso-occlusive Coils (II)."

Yet another embodiment of a stretch resistant coil includes a stretch resistant member, such as a fiber, which extends through at least a portion of a primary coil having proximal and distal ends. The stretch resistant member is attached to the primary coil at two axially separated locations to prevent or minimize axial stretching of the coil. One of these attachment locations is created with an anchor assembly disposed within the lumen of the coil. The anchor assembly takes the form of a coil that is incorporated into the windings of the primary coil. Such a device is disclosed in U.S. Patent Publication No. U.S. 2004/0002733, entitled "Integrated Anchor Coil in Stretch-Resistant Vaso-occlusive Coils."

Still another embodiment of a stretch resistant coil and delivery system takes the form of an interlocking coupling between a pusher member and a thin wire affixed to an embolic coil. The thin wire may be affixed to a distal, intermediate or proximal location on the coil and includes a ball shaped member fixedly attached to the proximal end of the wire. In order to position the coil at the treatment site, a pusher member with a ball member affixed to its distal end releasably interlocks with the ball member at the proximal end of the stretch resistant member. Such a device is disclosed in U.S. Pat. No. 5,304,195, entitled, "Detachable Pusher-Vasoocclusive Coil Assembly with Interlocking Coupling."

Another embodiment of a stretch resistant embolic coil includes an embolic coil with a stretch resisting member extending through its lumen and being attached to the coil in at least two locations. The stretch resistant member is somewhat loose within the lumen of the embolic coil, and the coil may take on a secondary shape after release within the body. Such a device is disclosed in U.S. Pat. No. 5,853,418, entitled, "Stretch Resistant Vaso-occlusive Coils (II)."

Even another embodiment of a stretch resistant embolic coil includes a coil with proximal and distal ends reinforced with a stretch resistant member extending therethrough. The distal end of the stretch resistant member is fixedly attached at the distal end of the coil, and the proximal end of the stretch resistant member is detachably mounted on an elongated pusher member at its distal end. Such a device is disclosed in U.S. Patent Publication No. 2005/0043755, entitled, "Vasoocclusive Coil with Enhanced Therapeutic Strand Structure."

Yet another embodiment of a stretch resistant embolic coil includes a wire that is wrapped with a polymer and is helically wound. A stretch resistant member may extend though the lumen of the coil and is attached to at least two points on the coil. Such a device is disclosed in U.S. Pat. No. 6,280,457, entitled, "Polymer Covered Vaso-occlusive Devices and Methods of Producing Such Devices."

Still another embodiment of a stretch resistant embolic coil includes an outer coil and at least one inner co-axial member. When the outer coil is subjected to axial tension it lengthens axially and contracts radially. The radial contraction is resisted by the inner co-axial member. Such a device is disclosed in U.S. Patent Publication No. 2004/0006363, entitled, "Coaxial Stretch Resistant Vaso-Occlusive Device."

SUMMARY OF THE INVENTION

The present invention is directed toward a vasoocclusive device deployment system for use in placing an embolic device at a preselected site within a vessel. In accordance with an aspect of the present invention, the deployment system includes an elongated flexible delivery catheter and an elongated flexible deployment catheter slidably disposed within the lumen of the delivery catheter. Also included is an embolic coil, which is preferably helically wound. A stretch resistant fiber is bonded to the coil at the distal end of the coil and extends through the lumen of the coil. Portions of the stretch resistant fiber have periodic undulations interspersed between straight portions, and the proximal end of the fiber is bonded to the proximal end of the embolic device. Additionally, the stretch resistant fiber may be attached to the embolic coil at additional points along the length of the coil.

In accordance with another aspect of the present invention, a headpiece is mounted on the proximal end of the embolic coil and is also disposed in fluid tight engagement within the lumen of the distal section of the deployment catheter. Additionally, a source of fluid pressure is coupled to the proximal section of the deployment catheter for applying a fluid pressure to the headpiece to thereby release the embolic coil from the deployment catheter. The distal section of the deployment catheter may be formed of a material which exhibits the characteristic that when fluid pressure is applied to the lumen of the deployment catheter the distal section of the deployment catheter expands outward, to release the headpiece.

In accordance with yet another aspect of the present invention, an embolic device includes an embolic coil that is helically wound. A stretch resistant fiber is bonded to the distal end of the embolic coil, extends through the lumen of the embolic coil, and the proximal end of the stretch resistant fiber is bonded to the proximal end of the embolic coil. The stretch resistant fiber has periodic undulations along its length, preferably helically wound, which are interspersed between straight portions. Additionally, the stretch resistant fiber may be attached to the embolic coil at additional points along the length of the coil. A headpiece is mounted on the proximal end of the embolic coil in order to couple the embolic device to a delivery system.

In accordance with still another aspect of the present invention, an embolic device includes an embolic coil that is helically wound. A stretch resistant fiber is bonded to the distal end of the embolic coil, extends through the lumen of the embolic coil, and is bonded to the proximal end of the embolic coil. The stretch resistant fiber has undulations along its length interspersed between straight portions. These undulations may be randomly placed along the fiber or alternately may be periodic in nature. The undulations may also be helically wound. Additionally, the stretch resistant fiber may be attached to the embolic coil at additional points along the length of the coil. A headpiece is mounted on the proximal end of the coil in order to couple the device to a deployment system.

These aspects of the invention and the advantages thereof will be more clearly understood from the following descriptions and drawings of a preferred embodiment of the present invention:

DESCRIPTION OF THE PREFERRED EMBODIMENT

Figure 1:
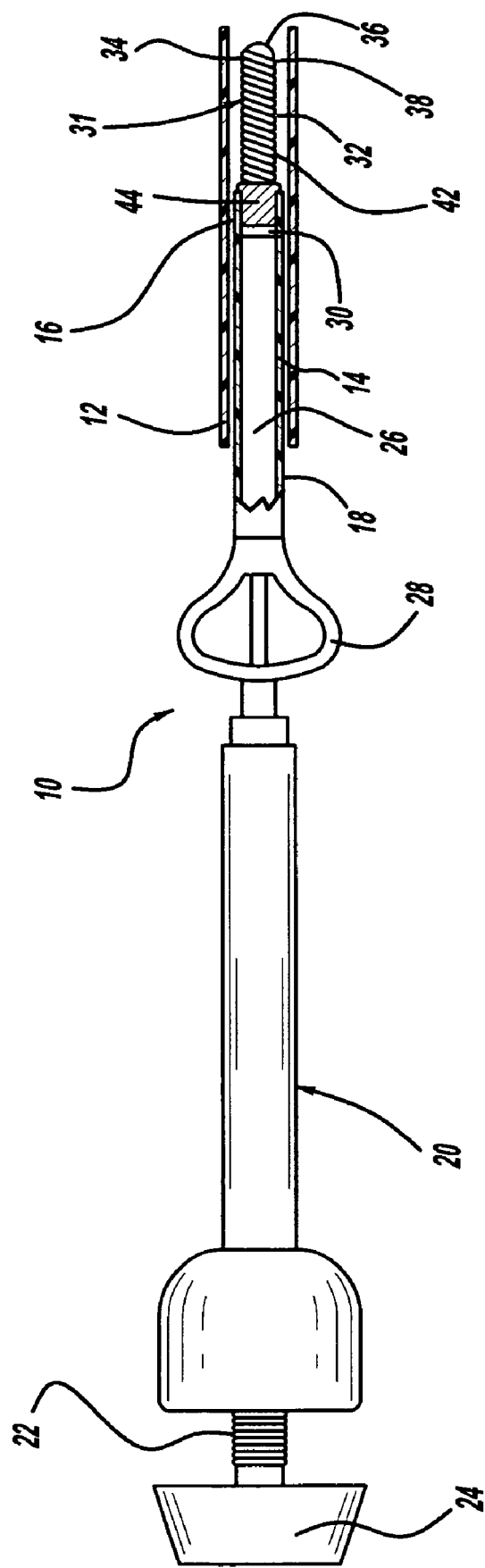
FIG. 1 is an enlarged, partially sectional view of one embodiment of a stretch resistant vasoocclusive device deployment system in accordance with the present invention; and, FIG. 2 is an enlarged sectional view of the stretch resistant embolic device shown in FIG. 1.

FIG. 1 generally illustrates one embodiment of a stretch resistant vasoocclusive device deployment system 10 of the present invention, including an elongated flexible delivery catheter 12 having an elongated flexible deployment catheter 14 slidably disposed within the lumen 16 of the delivery catheter 12, and a stretch resistant embolic device 31 is situated within the lumen 26 of the distal section 30 of the deployment catheter 14. A source of fluid pressure is coupled to the proximal section 18 of the deployment catheter 14 and preferably takes the form of a syringe 20. The syringe 20 includes a threaded piston 22, which is controlled by a handle 24 to thereby infuse fluid into the lumen 26 of the deployment catheter 14. Also as illustrated, the proximal end 18 of the deployment catheter 14 includes a winged hub 28 which aides in the insertion of the deployment catheter into the vasculature of the body.

The stretch resistant embolic device 31 is disposed within the lumen 26 of the distal section 30 of the deployment catheter 14. The stretch resistant embolic device 31 includes a cylindrical embolic coil 32 having an atraumatic distal bead 36 bonded to the distal end of the coil 32. Additionally, a headpiece 44 is mounted on the proximal end 42 of the coil 32 which, in turn, is disposed in fluid tight engagement within the lumen 26 of the distal section 30 of the deployment catheter 14, thereby coupling the stretch resistant embolic device 31 to the deployment catheter.

When the embolic coil 32 is at the desired treatment site, the handle 24 is manipulated to advance the threaded piston 22 which thereby infuses fluid into the lumen of the deployment catheter 14. The fluid is advanced through the lumen 26 of the deployment catheter 14 and pressure is applied to the proximal end of the headpiece 44 and thereby the embolic device to displace it from its position within the distal section 30 of the deployment catheter 14.

If desired, the distal section 30 of the deployment catheter 14 may be formed from a material having a different durometer from that used to form the proximal section 18. For example, the proximal section 18 of the deployment catheter 14 may be formed of Pebax material having a durometer in the range of about 62 D to 75 D. The proximal section will then be sufficiently flexible to traverse the vasculature of the human body, but also sufficiently rigid such that when a fluid pressure of approximately 400 psi is applied to the interior of this section of the deployment catheter there is little, if any, radial expansion of the walls of this section of the deployment catheter. In contrast, the distal section 30 of the deployment catheter 14 may be formed from a polymer material with a relatively low durometer. The distal section 30 of the deployment catheter 14 is preferably formed from a block copolymer, such as Pebax, having a durometer in a range of 25 D to 55 D with a preferred durometer of 40 D.

The lower durometer material used to form the distal section 30 of the deployment catheter 14 exhibits the characteristic that when a fluid pressure of approximately 400 psi is applied to the interior, the walls of the distal end 30 expand radially, somewhat similar to the action of a balloon inflating, to thereby release the headpiece 44 of the embolic coil 32.

Figure 2:
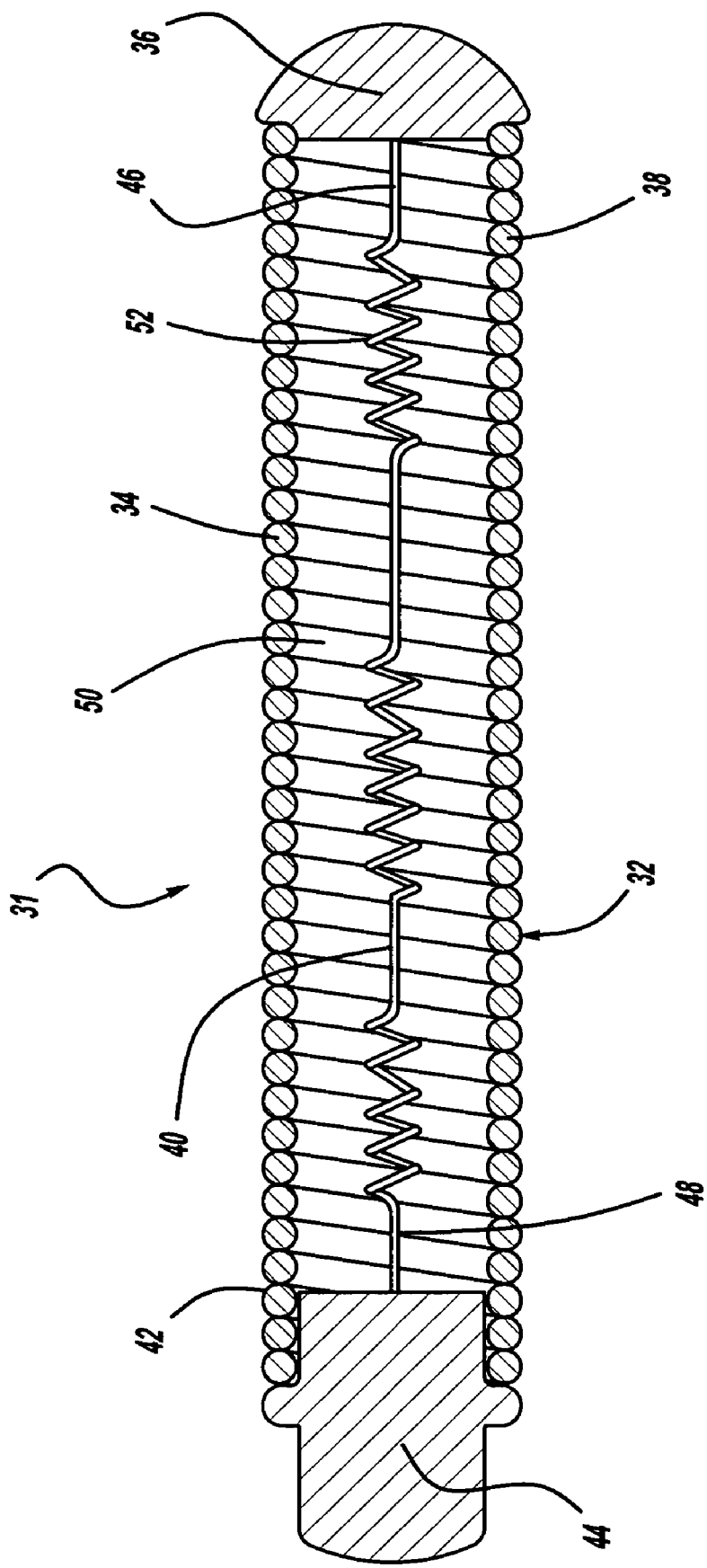

FIG. 2 illustrates in greater detail the stretch resistant embolic device 31. The stretch resistant embolic device 31 includes the embolic coil 32 which has the atraumatic distal bead 36 bonded to the distal end 38 of the coil 32. Also included is a stretch resistant fiber 40 which has its distal end 46 bonded to the distal end 38 of the coil 32. The stretch resistant fiber 40 extends through the lumen 50 of the embolic coil 32 and has periodic undulations 52 which are interrupted by extended straight portions. The proximal end 48 of the stretch resistant fiber 40 is attached to the proximal end 42 of the coil 32, or alternately to the headpiece 44 which is mounted on the proximal end 42 of the coil 32 and is coupled to the stretch resistant embolic device 31 to the deployment system 10.

More particularly, the embolic coil 32 is preferably formed with loosely wound helical turns 34 dispersed between straight portions and is constructed from a radiopaque platinum tungsten alloy. The atraumatic distal bead 36 has a generally hemispherical shape and is formed from a plasma bead or a solder weld. The stretch resistant fiber 40 is preferably formed from a nitinol or platinum wire, but may also be formed from a polymer braid or filament. The periodic undulations 52 of the stretch resistant fiber 40 are formed by bending portions of the wire into the desired shape, such as a helical configuration. The bends in the stretch resistant fiber may also take the shape of a sinusoidal wave, randomly placed bends, or helical turns.

During placement of the embolic coil, fluid pressure is applied to dislodge the headpiece 44 and thereby the stretch resistant embolic device 31 from the deployment system 10. An important advantage of the present invention is that if it is determined that the embolic device 31 is improperly positioned, the embolic device may then be withdrawn from that location and placed at another location or even removed from the body altogether.

The stretch resistant fiber 40 facilitates repositioning of the embolic device 31, because it prevents the embolic coil 32 from stretching uncontrollably when it is pulled from the initial position. Once the embolic device 31 is released at the appropriate location, the stretch resistant fiber 40 has a limited mobility, which may dictate, in part, a secondary shape for the embolic device 31, after it is released from and no longer constrained by the deployment catheter.

Although the stretch resistant fiber 40 provides stretch resistance to the embolic device 31, another important advantage of the present invention is that the stretch resistant fiber 40, having portions with undulations or with helical windings increases the flexibility of the device. More specifically, when the stretch resistant embolic device 31 is pulled proximally the undulations 52 will straighten to allow some degree of stretching before the embolic device 31 is stretch resistant. In turn, these undulations will add flexibility to the embolic device 31 after it is released from the catheter such that the embolic device may take on a secondary shape after deployment.

As is apparent, there are numerous modifications of the preferred embodiment described above which will be readily apparent to one skilled in the art, such as many variations and modifications of the embolic coil including numerous coil winding configurations. There are also variations in the materials used to form the various components. Additionally, the shape and frequency of the undulations may be modified, and the frequency of attachment between the embolic coil and the stretch resistant member may also be increased in order to increase the stretch resistance of the stretch resistant embolic device 31. These modifications would be apparent to those having ordinary skill in the art to which this invention relates and are intended to be within the scope of the claims which follow.

That which is claimed is:

1. A vasoocclusive embolic device and a vasoocclusive embolic deployment system for use in placing an embolic device at a preselected site within a vessel comprising:
    an elongated flexible delivery catheter having proximal and distal sections and a lumen extending therethrough;
    an elongated flexible deployment catheter having proximal and distal sections and a lumen extending therethrough and being slidably disposed within the lumen of the elongated flexible delivery catheter;
    an embolic coil having proximal and distal ends and a lumen extending therethrough;
    a stretch resistant fiber having periodic flexible undulations that permit some degree of stretching along at least a portion of the length of the fiber interspersed between straight portions and having proximal and distal ends, said stretch resistant fiber extending through the lumen of the embolic coil, said distal end of said stretch resistant fiber being attached to the distal end of the embolic coil, said proximal end of said stretch resistant fiber being attached to the proximal end of the embolic coil;
    a headpiece mounted on the proximal end of the embolic coil and being disposed in a fluid tight engagement within the lumen of the distal section of the deployment catheter; and,
    a source of fluid pressure coupled to the proximal section of the deployment catheter for applying a fluid pressure to the lumen of said deployment catheter for releasing the embolic coil from the deployment catheter; wherein a portion of the embolic coil surrounding both the undulations and straight portions is helical.

2. A vasoocclusive embolic device deployment system as defined in claim 1, wherein the periodic undulations along the length of the stretch resistant fiber take the form of a loosely wound helical coil.

3. A vasoocclusive embolic device deployment system as defined in claim 2, wherein the embolic coil comprises a helically wound coil.

4. A vasoocclusive embolic device deployment system as defined in claim 1, wherein the stretch resistant fiber is attached to the embolic coil at additional points between the proximal and distal ends of the embolic coil.

5. A vasoocclusive embolic device deployment system as defined in claim 1, wherein the distal section of the deployment catheter is formed of a material that exhibits the characteristic that when fluid pressure is applied to the lumen of the deployment catheter said distal section of the deployment catheter expands outward to release the headpiece.

6. A vasoocclusive embolic device for use in placement at a treatment site within a vessel comprising:
    an embolic coil having proximal and distal sections and a lumen extending therethrough;
    a stretch resistant fiber having periodic flexible undulations that permit some degree of stretching along at least a portion of the length of the fiber interspersed between straight portions and having proximal and distal ends, said stretch resistant fiber extending through the lumen of the embolic coil, said distal end of said stretch resistant fiber being attached to the distal section of the embolic coil, said proximal end of said stretch resistant fiber being attached to the proximal section of the embolic coil; and,
    a headpiece mounted on the proximal section of the coil which serves to couple the embolic coil to an embolic delivery system; wherein a portion of the embolic coil surrounding both the undulations and straight portions is helical.

7. A vasoocclusive embolic device as defined in claim 6, wherein the periodic undulations along the length of the stretch resistant fiber take the form of a loosely wound helical coil.

8. A vasoocclusive embolic device as defined in claim 6, wherein the embolic coil comprises a helically wound coil.

9. A vasoocclusive embolic device as defined in claim 6, wherein the stretch resistant fiber is attached to the embolic coil at additional points between the proximal and distal sections of the embolic coil.

10. A vasoocclusive embolic device for use in placement at a treatment site within a vessel comprising:
- an embolic coil having proximal and distal ends and a lumen extending therethrough; and
- a stretch resistant fiber having flexible periodic undulations that permit some degree of stretching along at least a portion of the length of the fiber interspersed between straight portions and having proximal and distal ends, said stretch resistant fiber extending through the lumen of the embolic coil, said distal end of said stretch resistant fiber being attached to the distal end of the embolic coil, said proximal end of said stretch resistant fiber being attached to the proximal end of the embolic coil; wherein a portion of the embolic coil surrounding both the undulations and straight portions is helical.

11. A vasoocclusive embolic device as defined in claim 10, wherein the undulations along the length of the stretch resistant fiber are spaced between straight portions of the stretch resistant fiber.

12. A vasoocclusive embolic device as defined in claim 10, wherein the undulations along the length of the stretch resistant fiber are periodic along the length of the fiber.

13. A vasoocclusive embolic device as defined in claim 10, wherein the undulations along the length of the stretch resistant fiber are helically wound coils.

14. A vasoocclusive embolic device as defined in claim 10, wherein the embolic coil comprises a helically wound embolic coil.

15. A vasoocclusive embolic device as defined in claim 10, wherein the stretch resistant fiber is attached to the embolic coil at additional points between the proximal and distal ends of the embolic coil.

* * * * *